(12) United States Patent
Key et al.

(10) Patent No.: US 7,692,040 B2
(45) Date of Patent: Apr. 6, 2010

(54) PROCESS FOR THE PRODUCTION OF ACETIC ACID

(75) Inventors: Lesley Ann Key, East Riding of Yorkshire (GB); Marc John Payne, Oxfordshire (GB); Andrew David Poole, East Riding of Yorkshire (GB)

(73) Assignee: BP Chemicals Limited, Middlesex (GB)

( * ) Notice: Subject to any disclaimer, the term of this patent is extended or adjusted under 35 U.S.C. 154(b) by 1005 days.

(21) Appl. No.: 10/528,387

(22) PCT Filed: Sep. 3, 2003

(86) PCT No.: PCT/GB03/03834

§ 371 (c)(1),
(2), (4) Date: Sep. 21, 2005

(87) PCT Pub. No.: WO2004/026805

PCT Pub. Date: Apr. 1, 2004

(65) Prior Publication Data

US 2006/0122422 A1     Jun. 8, 2006

(30) Foreign Application Priority Data

Sep. 19, 2002    (GB) ................................. 0221800.6

(51) Int. Cl.
*C07C 51/12*     (2006.01)

(52) U.S. Cl. ...................................................... 562/519
(58) Field of Classification Search .................. 562/519
See application file for complete search history.

(56) References Cited

FOREIGN PATENT DOCUMENTS

| EP | 0 749 948 A1 | 12/1996 |
| EP | 0 846 647 A1 | 6/1998 |

OTHER PUBLICATIONS

Sunley, G.J., et al; "High productivity methanol carbonylation catalysis using iridium The Cativa™ process for the manufacture of acetic acid"; vol. 58, No. 4, pp. 293-307 (2000); XP002264805.

*Primary Examiner*—Taylor Victor Oh
(74) *Attorney, Agent, or Firm*—Nixon & Vanderhye

(57) ABSTRACT

A process for the production of acetic acid by carbonylating methanol and/or a reactive derivative thereof with carbon monoxide in at least one carbonylation reaction zone containing a liquid reaction composition comprising an iridium carbonylation catalyst, methyl iodide co-catalyst, a finite concentration of water, acetic acid, methyl acetate, at least one promoter selected from ruthenium, osmium and rhenium and at least one catalyst system stabiliser selected from indium, cadmium, mercury, gallium and zinc and wherein the molar ratio of iridium:promoter:stabiliser in the liquid reaction composition is maintained in the range 1:(>2 to 15):(0.25 to 12).

15 Claims, No Drawings

PROCESS FOR THE PRODUCTION OF ACETIC ACID

This application is the U.S. National Phase of International Application PCT/GB2003/003834, filed 3 Sep. 2003, which designated the U.S. PCT/GB2003/003834 claims priority to British Application No. 0221800.6 filed 19 Sep. 2002. The entire content of these applications are incorporated herein by reference.

The present invention relates to a process for the production of acetic acid and in particular to a process for the production of acetic acid by the carbonylation of methanol and/or a reactive derivative thereof in the presence of a promoted iridium catalyst.

The production of acetic acid by the carbonylation of methanol in the presence of an iridium catalyst and a promoter such as ruthenium is described, for example, in EP-A-0752406, EP-A-0849248, EP-A-0849249, and EP-A-1002785.

EP-A-0643034 describes a process for the carbonylation of methanol and/or a reactive derivative thereof in the presence of acetic acid, an iridium catalyst, methyl iodide, at least a finite concentration of water, methyl acetate and a promoter selected from ruthenium and osmium.

EP-A-0 749 948 describes a process for the carbonylation of an alkyl alcohol such as methanol and/or a reactive derivative thereof to produce the corresponding carboxylic acid and/or ester in the presence of an iridium catalyst, an alkyl halide, water and at least one promoter selected from cadmium, mercury, zinc, gallium, indium and tungsten, optionally with a co-promoter selected from ruthenium, osmium and rhenium.

In a carbonylation process employing a promoted iridium catalyst, it has generally been found that the higher the concentration of promoter, the greater the rate of reaction. However, it has also been found that where the carbonylation process is carried out using relatively high concentrations of promoter precipitation of the catalyst system (iridium and promoter) may occur.

In addition, under certain operating conditions, such as during carbon monoxide deficient conditions, precipitation of the catalyst system may occur.

Thus, there remains a need for an iridium-catalysed promoted carbonylation process in which catalyst system stability is improved and, in particular, an iridium-catalysed promoted carbonylation process in which catalyst system stability is improved and in which the carbonylation rate is also at least maintained or increased.

The present invention solves the technical problem defined above by employing at least one of indium, cadmium, mercury, zinc and gallium in the liquid reaction composition.

Accordingly, the present invention provides a process for the production of acetic acid by carbonylating methanol and/or a reactive derivative thereof with carbon monoxide in at least one carbonylation reaction zone containing a liquid reaction composition comprising an iridium carbonylation catalyst, methyl iodide co-catalyst, a finite concentration of water, acetic acid, methyl acetate, at least one promoter selected from ruthenium, osmium and rhenium and at least one catalyst system stabiliser selected from indium, cadmium, mercury, gallium and zinc and wherein the molar ratio of iridium:promoter:stabiliser in the liquid reaction composition is maintained in the range 1:(>2 to 15):(0.25 to 12).

The present invention further provides for the use of at least one of indium, cadmium, mercury, gallium and zinc as a catalyst system stabiliser in a process for the production of acetic acid which process comprises carbonylating methanol and/or a reactive derivative thereof with carbon monoxide in at least one carbonylation reaction zone containing a liquid reaction composition comprising an iridium carbonylation catalyst, methyl iodide co-catalyst, a finite concentration of water, acetic acid, methyl acetate, at least one promoter selected from ruthenium, osmium and rhenium; and at least one catalyst system stabilizer selected from indium, cadmium, mercury, gallium and zinc and wherein the molar ratio of iridium:promoter:stabiliser in the liquid reaction composition is maintained in the range 1:(>2 to 15):(0.25 to 12).

The present invention allows the stability of the catalyst system to be improved whilst maintaining or increasing the carbonylation rate.

Advantageously, the present invention allows the process to be operated at lower ratios of promoter:iridium, thereby reducing the amount of expensive promoter needed.

In addition, the present invention allows the process to be operated at lower iridium concentrations whilst at least maintaining the carbonylation rate.

The reaction zone may comprise a conventional liquid-phase carbonylation reaction zone.

Preferably, two reaction zones are used, the first and second reaction zones being maintained in separate reaction vessels with means for withdrawing from the first reaction vessel and passing to the second reaction vessel liquid reaction composition from the first reaction vessel with dissolved and/or entrained carbon monoxide. Such a separate second reaction vessel may comprise a section of pipe between the first reaction vessel and a liquid reaction composition flashing valve. Preferably the pipe is liquid full. Typically the pipe's length to diameter ratio may be about 12:1, though length to diameter ratios both higher and lower than this may be employed.

Typically, at least a portion of the liquid reaction composition together with dissolved and/or entrained carbon monoxide is withdrawn from the first reaction zone and at least a portion of the withdrawn liquid and dissolved and/or entrained carbon monoxide passed to a second reaction zone. Preferably substantially all the liquid reaction composition together with dissolved and/or entrained carbon monoxide withdrawn from the first reaction zone is passed to the second reaction zone.

The pressure of the carbonylation reaction in the first reaction zone is suitably in the range 15 to 200 barg, preferably 15 to 100 barg, more preferably 15 to 50 barg and yet more preferably 18 to 35 barg. The temperature of the carbonylation reaction in the first reaction zone is suitably in the range 100 to 300° C., preferably in the range 150 to 220° C.

The second reaction zone may be operated at a reaction temperature in the range 100 to 300° C., preferably in the range 150 to 230° C. The second reaction zone may be operated at a temperature higher than the first reaction zone, typically up to 20° C. higher. The second reaction zone may be operated at a reaction pressure in the range 10 to 200 barg, preferably in the range 15 to 100 barg. Preferably, the reaction pressure in the second reaction zone is equal to or less than the reaction pressure in the first reaction zone. The residence time of liquid reaction composition in the second reaction zone is suitably in the range 5 to 300 seconds, preferably 10 to 100 seconds.

The carbon monoxide reactant for the carbonylation reactions may be essentially pure or may contain inert impurities such as carbon dioxide, methane, nitrogen, noble gases, water and $C_1$ to $C_4$ paraffinic hydrocarbons. The presence of hydrogen in the carbon monoxide and generated in situ by the water gas shift reaction is preferably kept low, for example, less than 1 bar partial pressure, as its presence may result in the formation of hydrogenation products. The partial pressure of carbon monoxide in the first and second reaction zones is suitably independently in the range 1 to 70 bar, preferably 1 to 35 bar and more preferably 1 to 15 bar.

There may be introduced to the second reaction zone carbon monoxide in addition to that introduced to the second reaction zone as dissolved and/or entrained carbon monoxide. Such additional carbon monoxide may be co-joined with the first liquid reaction composition prior to introduction to the second reaction zone and/or may be fed separately to one or more locations within the second reaction zone. Such additional carbon monoxide may contain impurities, such as for example $H_2$, $N_2$, $CO_2$ and $CH_4$. The additional carbon monoxide may be comprised of high pressure off-gas from the first reaction zone which could advantageously allow the first reaction zone to be operated at a higher CO pressure with the resulting higher flow of carbon monoxide being fed to the second reaction zone. Additionally it could eliminate the requirement for a high pressure off-gas treatment.

The additional carbon monoxide may also be comprised of another carbon monoxide-containing gas stream such as for example a carbon monoxide-rich stream from another plant.

Preferably greater than 10%, more preferably greater than 25%, even more preferably greater than 50%, for example at least 95%, of the dissolved and/or entrained carbon monoxide in the withdrawn reaction composition from the first reaction zone is consumed in the second reaction zone.

In the process of the present invention, suitable reactive derivatives of methanol include methyl acetate, dimethyl ether and methyl iodide. A mixture of methanol and reactive derivatives thereof may be used as reactants in the process of the present invention. Water is required as co-reactant for ether or ester reactants Preferably, methanol and/or methyl acetate are used as reactants.

At least some of the methanol and/or reactive derivative thereof will be converted to, and hence present as, methyl acetate in the liquid reaction composition by reaction with the carboxylic acid product or solvent. Preferably, the concentrations of methyl acetate in the liquid reaction compositions in the first and second reaction zones are independently in the range 1 to 70% by weight, more preferably 2 to 50% by weight, most preferably 3 to 35% by weight Water may be formed in situ in the liquid reaction compositions, for example, by the esterification reaction between methanol reactant and acetic acid product. Water may be introduced independently to the first and second carbonylation reaction zones together with or separately from other components of the liquid reaction compositions. Water may be separated from other components of reaction compositions withdrawn from the reaction zones and may be recycled in controlled amounts to maintain the required concentration of water in the liquid reaction compositions. Preferably, the concentrations of water in the liquid reaction compositions in the first and second reaction zones are independently in the range 0.1 to 20% by weight, more preferably 1 to 15% by weight, yet more preferably 1 to 10% by weight.

Preferably, the concentration of methyl iodide co-catalyst in the liquid carbonylation reaction compositions in the first and second reaction zones is independently in the range 1 to 20% by weight, preferably 2 to 16% by weight.

The iridium catalyst in the liquid reaction compositions in the first and second reaction zones may comprise any iridium-containing compound which is soluble in the liquid reaction compositions. The iridium catalyst may be added to the liquid reaction compositions in any suitable form which dissolves in the liquid reaction compositions or is convertible to a soluble form. Preferably the iridium may be used as a chloride free compound such as acetates which are soluble in one or more of the liquid reaction composition components, for example water and/or acetic acid and so may be added to the reaction as solutions therein. Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(CO)_2I_2]^-H^+$, $[Ir(CH_3)I_3(CO)_2]^-H^+$, $Ir_4(CO)_{12}$, $IrCl_3.4H_2O$, $IrBr_3.4H_2O$, $Ir_3(CO)_{12}$, iridium metal, $Ir_2O_3$, $IrO_2$, $Ir(acac)(CO)_2$, $Ir(acac)_3$, iridium acetate, $[Ir_3O(OAc)_6(H_2O)_3][OAc]$, and hexachloroiridic acid $H_2[IrCl_6]$, preferably, chloride-free complexes of iridium such as acetates, oxalates and acetoacetates.

Preferably, the concentration of the iridium catalyst in the liquid reaction compositions of the first and second reaction zones is independently in the range 100 to 6000 ppm by weight of iridium.

The liquid reaction compositions in the first and second reaction zones additionally comprises one or more promoters. Suitable promoters are selected from ruthenium, osmium and rhenium, and are more preferably selected from ruthenium and osmium. Ruthenium is the most preferred promoter. The promoter may comprise any suitable promoter metal-containing compound which is soluble in the liquid reaction composition. The promoter may be added to the liquid reaction composition for the carbonylation reaction in any suitable form which dissolves in the liquid reaction composition or is convertible to soluble form.

Examples of suitable ruthenium-containing compounds which may be used as sources of promoter include ruthenium (III) chloride, ruthenium (III) chloride trihydrate, ruthenium (IV) chloride, ruthenium (III) bromide, ruthenium metal, ruthenium oxides, ruthenium (III) formate, $[Ru(CO)_3I_3]-H+$, $[Ru(CO)_2I_2]_n$, $[Ru(CO)_4I_2]$, $[Ru(CO)_3I_2]_2$, tetra(aceto)chlororuthenium(II,III), ruthenium (III) acetate, ruthenium (III) propionate, ruthenium (III) butyrate, ruthenium pentacarbonyl, triruthenium dodecacarbonyl and mixed ruthenium halocarbonyls such as dichlorotricarbonylruthenium (II) dimer, dibromotricarbonylruthenium (II) dimer, and other organoruthenium complexes such as tetrachlorobis (4-cymene)diruthenium(II), tetrachlorobis(benzene)diruthenium(II), dichloro(cycloocta-1,5diene) ruthenium (II) polymer and tris (acetylacetonate)ruthenium (III).

Examples of suitable osmium-containing compounds which may be used as sources of promoter include osmium (III) chloride hydrate and anhydrous, osmium metal, osmium tetraoxide, triosmiumdodecacarbonyl, $[Os(CO)_4I_2]$, $[Os(CO)_3I_2]_2$, $[Os(CO)_3I_3]-H+$, pentachloro-μ-nitrodiosmium and mixed osmium halocarbonyls such as tricarbonyldichloroosmium (II) dimer and other organoosmium complexes.

Examples of suitable rhenium-containing compounds which may be used as sources of promoter include $Re_2(CO)_{10}$, $Re(CO)_5Cl$, $Re(CO)_5Br$, $Re(CO)_5I$, $ReCl_3.xH_2O$, $[Re(CO)_4I]_2$, $Re(CO)_4I_2]^-H^+$ and $ReCl_5.yH_2O$.

Preferably, the promoter is present in an effective amount up to the limit of its solubility in the liquid reaction compositions and/or any liquid process streams recycled to the carbonylation reactor from the acetic acid recovery stage. The promoter is suitably present in the liquid reaction compositions at a molar ratio of promoter to iridium of [greater than 2 to 15]:1, preferably [greater than 2 to 10]:1, more preferably [4 to 10]:1. A suitable promoter concentration is less than 8000 ppm, such as 400 to 7000 ppm.

The indium, cadmium, mercury, zinc and/or gallium catalyst system stabiliser may comprise any indium, cadmium, mercury, zinc or gallium containing compound which is soluble in the liquid reaction compositions. The catalyst system stabiliser may be added to the liquid reaction composition in the first and/or second reaction zone in any suitable form which dissolves in the liquid reaction composition or is convertible to a soluble form.

Examples of suitable indium-containing compounds which may be used include indium acetate, $InCl_3$, $InI_3$, $InI$, $In(OH)_3$ and indium acetylacetonate. Preferably, the indium-containing compound is indium acetate or $InI_3$.

Examples of suitable cadmium-containing compounds which may be used include $Cd(OAc)_2$, $CdI_2$, $CdBr_2$, $CdCl_2$, $Cd(OH)_2$, and cadmium acetylacetonate.

Preferably, the cadmium-containing compound is cadmium acetate or $CdI_2$.

Examples of suitable mercury-containing compounds which may be used include $Hg(OAc)_2$, $HgI_2$, $HgBr_2$, $HgCl_2$, $Hg_2I_2$, and $Hg_2Cl_2$. Preferably, the mercury-containing compound is mercury acetate or $HgI_2$.

Examples of suitable zinc-containing compounds which may be used include $Zn(OAc)_2$, $Zn(OH)_2$, $ZnI_2$, $ZnBr_2$, $ZnCl_2$, and zinc acetylacetonate. Preferably, the zinc-containing compound is zinc acetate or $ZnI_2$.

Examples of suitable gallium-containing compounds which may be used include gallium acetylacetonate, gallium acetate, $GaCl_3$, $GaBr_3$, $GaI_3$, $Ga_2Cl_4$ and $Ga(OH)_3$. Preferably, the gallium-containing compound is gallium acetate or $GaI_3$.

The molar ratio of catalyst system stabiliser:iridium in the liquid reaction compositions of the first and second reaction zones is independently in the range (0.25 to 12):1, preferably (1 to 12):1, for example (1 to 8):1

The molar ratio of iridium:promoter:catalyst system stabiliser in the liquid reaction compositions is independently in the range 1:(greater than 2 to 15):(0.25 to 12). Suitably, the molar ratio of iridium:promoter:catalyst system stabiliser may be 1:(greater than 2 to 10):(0.25 to 12), such as 1:(greater than 2 to 10):(1 to 12), for example, 1:(3 to 10):(0.25 to 12), 1:(4 to 10):(0.25 to 12), 1:(4 to 10):(1 to 12), 1:(4 to 10):(1 to 8) and preferably, 1:(3 to 10):(1 to 10), 1:(greater than 4 to 10):(1 to 10), especially, 1:(greater than 4 to 10):(1 to 8).

In a preferred embodiment of the present invention, the promoter is ruthenium and the molar ratio of iridium:ruthenium:catalyst system stabiliser in the liquid reaction compositions is independently in the range 1:(greater than 2 to 15):(0.25 to 12). Suitably, the molar ratio of iridium:ruthenium:catalyst system stabiliser may be 1:(greater than 2 to 10):(0.25 to 12), such as 1:(greater than 2 to 10):(1-12), for example, 1:(4 to 10):(0.25 to 12), 1:(4 to 10):(1 to 12), 1:(4 to 10):(1 to 8) and preferably, 1:(greater than 4 to 10):(1 to 10), especially, 1:(greater than 4 to 10):(1 to 8).

A suitable catalyst system stabiliser concentration in the liquid reaction compositions of the first and second reaction zones is independently less than 9000 ppm, such as 300 to 8000 ppm, for example 300 to 5000 ppm.

Preferably, the iridium, promoter and the indium, cadmium, mercury, gallium and/or zinc-containing compound are free of impurities which provide or generate in-situ ionic iodides which may inhibit the reaction, for example, alkali or alkaline earth metal or other metal salts.

Ionic contaminants such as, for example, (a) corrosion metals, particularly nickel, iron and chromium and (b) phosphines or nitrogen containing compounds or ligands which may quaternise in-situ, should be kept to a minimum in the liquid reaction composition as these will have an adverse effect on the reaction by generating $I^-$ in the liquid reaction composition which has an adverse effect on the reaction rate. Similarly, contaminants such as alkali metal iodides, such as lithium iodide, should be kept to a minimum. Corrosion metal and other ionic impurities may be reduced by the use of a suitable ion-exchange resin bed to treat the reaction composition or preferably the catalyst recycle stream. Preferably, ionic contaminants are kept below a concentration at which they would generate 500 ppm $I^-$, preferably less than 250 ppm $I^-$ in the liquid reaction composition.

Acetic acid product may be recovered from the second reaction zone and optionally together with or separately from the first reaction zone by flash separation. In flash separation liquid reaction composition is passed to a flashing zone via a flashing valve. The flash separation zone may be an adiabatic flash vessel or may have additional heating means. In the flash separation zone a liquid fraction comprising the majority of the iridium catalyst and the majority of the promoter and stabiliser salt is separated from a vapour fraction comprising acetic acid, carbonylatable reactant, water and methyl iodide carbonylation co-catalyst and non-condensable gases such as nitrogen, carbon monoxide, hydrogen and carbon dioxide; the liquid fraction being recycled to the first reaction zone and the vapour fraction being passed to one or more distillation zones. In a first distillation zone acetic acid product is separated from the light components (methyl iodide and methyl acetate). The light components are removed overhead, and recycled to the first and/or second reaction zones. Also removed overhead is a low pressure off-gas comprising the non-condensable gases such as nitrogen, carbon monoxide, hydrogen and carbon dioxide. Such a low-pressure off-gas stream may be passed through an off-gas treatment section to remove condensable materials such as methyl iodide, prior to being vented to atmosphere, for example, via a flare.

The acetic acid produced by the process according to the present invention may be further purified by conventional processes, for example further distillation to remove impurities such as water, unreacted carbonylation reactant and/or ester derivative thereof and higher-boiling by-products.

The process of the present invention may be performed as a batch or as a continuous process, preferably as a continuous process.

The present invention will now be illustrated by way of example only and with reference to the following Examples.

General Reaction Method

All experiments were performed in either a 300 cm³ zirconium or a 300 cm³ Hastelloy autoclave, equipped with a stirrer and a liquid injection facility. Ruthenium acetate solution (18.7 g, approximately 5 wt % ruthenium), a catalyst system stabiliser compound (when used) and acetic acid (approx. 10.0 g) were placed into the autoclave base. The autoclave was pressure tested to 32 barg with nitrogen, flushed twice with nitrogen at 20 barg and then three times with carbon monoxide up to 10 barg. An initial charge consisting of methyl acetate (approx 48.0 g) acetic acid (approx 34.0 g), methyl iodide (approx 13.3 g) and water (approx 11.0 g) was placed into the autoclave, which was then repurged with carbon monoxide and vented slowly to prevent loss of volatiles.

Carbon monoxide (8 barg) was fed into the autoclave which was then heated, with stirring (1500 rpm) to 190° C. The catalyst injection system was primed with approx 6.3 g of iridium acetate solution (approx. 5 wt % iridium) and acetic acid (approx 8.7 g) and injected with an overpressure of carbon monoxide to bring the autoclave pressure to 28 barg.

The reaction rate was monitored by drop in carbon monoxide pressure from a ballast vessel, typically pressured to 82 barg. The autoclave was maintained at a constant temperature of 190° C. and pressure of 28 barg throughout the reaction. After uptake of carbon monoxide from the ballast vessel had ceased the autoclave was isolated from the gas supply and cooled. After cooling, a gas analysis sample was taken, and the autoclave vented. The liquid components were discharged, and analysed for liquid by-products by known established gas chromatography methods. Detected components were quantified by integration of the component peaks relative to an external standard and expressed as parts per million (ppm) by weight. The major product in each of the batch carbonylation experiments was acetic acid.

The rate of gas uptake at a certain point in a reaction run was used to calculate the carbonylation rate, as number of moles of reactant consumed per litre of cold degassed reactor composition per hour (mol/l/h) at a particular reactor composition (total reactor composition based on a cold degassed volume)

The methyl acetate concentration was calculated during the course of the reaction from the starting composition, assuming that one mole of methyl acetate was consumed for every mole of carbon monoxide that was consumed. No allowance was made for organic components in the autoclave headspace.

Catalyst System Stability Test

On completion of the carbonylation reaction (that is when no carbon monoxide gas uptake could be observed), the reaction solution was allowed to cool to room temperature. The autoclave was then depressurized and a 25 ml sample of cooled reaction solution was transferred from the autoclave to a Fischer-Porter tube. The tube was then sealed and pressurized with nitrogen to 0.5 barg and heated with stirring to 130° C. for 5 hours before cooling to room temperature and venting.

The formation or otherwise of a precipitate was determined by visual inspection of the tube contents.

EXAMPLES

Experiment A

A baseline experiment was performed with the autoclave charged with methyl acetate (47.96 g) acetic acid (44.1 g) ruthenium acetate solution (18.7 g) water (11.0 g) methyl iodide (12.59 g). The catalyst solution consisted of an iridium solution (6.31 g) with acetic acid (8.7 g). The approximate ratio of iridium to ruthenium was 1:6. The rate of reaction at a calculated reaction composition of 12% methyl acetate and catalyst system stability results are shown in Table 1.

Experiment B

A baseline experiment was performed with the autoclave charged with methyl acetate (48.01 g) acetic acid (43.1 g) ruthenium acetate solution (6.2 g) water (13.24 g) methyl iodide (13.34 g). The catalyst solution consisted of an iridium solution (6.31 g) with acetic acid (8.72 g). The approximate ratio of iridium to ruthenium was 1:2. The rate of reaction at a calculated reaction composition of 12% methyl acetate and catalyst system stability results are shown in Table 1.

Example 1

Experiment A was repeated except that the autoclave was also charged with 0.86 g $InI_3$. The rate of reaction at a calculated reaction composition of 12% methyl acetate and catalyst system stability results are shown in Table 1.

Example 2

Experiment A was repeated except that the autoclave was also charged with 1.73 g of $InI_3$. The rate of reaction at a calculated reaction composition of 12% methyl acetate and catalyst system stability results are shown in Table 1.

Example 3

Experiment A was repeated except that the autoclave was also charged with 0.51 g of $In(OAc)_3$. The rate of reaction at a calculated reaction composition of 12% methyl acetate and catalyst system stability results are shown in Table 1.

Example 4

Experiment A was repeated except that the autoclave was charged with 6.92 g of ruthenium solution and 1.013 g of $In(OAc)_3$. The main charge of the autoclave was adjusted to 48 g of methyl acetate, 44.9 g of acetic acid, 13.7 g of water and 13.3 g of methyl iodide. The catalyst solution consisted of an iridium solution (3.18 g) with acetic acid (8.7 g). The iridium to ruthenium to indium ratio was 0.5:2:2; however, the indium concentration was half that of Experiment B. The rate of reaction at a calculated reaction composition of 12% methyl acetate and catalyst system stability results are shown in Table 1.

TABLE 1

| Experiment | Ir:Ru:In Molar ratio | Rate at 12 wt % MeOAc mol/l/h | Precipitate formed |
| --- | --- | --- | --- |
| Experiment A | 1:6 | 24 | Yes |
| Example 1 | 1:6:1 | 27 | No |
| Example 2 | 1:6:2 | 29 | No |
| Example 3 | 1:6:1 | 26.5 | No |
| Experiment B | 1:2 | 19 | No |
| Example 4 | 0.5:2:2 | 19 | No |

In Table 1, it can be seen that from a comparison of Experiment A (no indium present) with Examples 1-3 (indium present) that both catalyst stability and carbonylation rates are improved in Examples 1-3. It can also be seen that from a comparison of Experiment B (no indium present) with Example 4 (indium present and a reduction in iridium concentration) that the carbonylation rate is maintained in Example 4.

The invention claimed is:

1. A process for the production of acetic acid comprising carbonylating methanol and/or a reactive derivative thereof selected from the group consisting of methyl acetate, dimethyl ether and methyl iodide with carbon monoxide in at least one carbonylation reaction zone containing a liquid reaction composition comprising an iridium carbonylation catalyst, methyl iodide co-catalyst, a finite concentration of water, acetic acid, methyl acetate, at least one promoter selected from ruthenium, osmium and rhenium and at least one catalyst system stabiliser selected from indium, cadmium, mercury, gallium and zinc and wherein the molar ratio of iridium:promoter:stabiliser in the liquid reaction composition is maintained in the range 1:(>2 to 15):(0.25 to 12).

2. A process according to claim 1 wherein the molar ratio of iridium:promoter:stabiliser in the liquid reaction composition is maintained in the range 1:(>2 to 10):(1 to 12).

3. A process according to claim 1 wherein the molar ratio of iridium:promoter:stabiliser in the liquid reaction composition is maintained in the range 1:(3 to 10):(1 to 10).

4. A process according to claim 1 or claim 2 wherein the concentration of catalyst system stabiliser in the liquid reaction composition is less than 9000 ppm.

5. A process according to claim 1 or claim 2 wherein the catalyst system stabiliser is selected from the group consisting of iodides or acetates of indium, cadmium, mercury, gallium and zinc.

6. A process according to claim 1 or claim 2 wherein the promoter is ruthenium.

7. A process according to claim 1 or claim 2 wherein the concentration of promoter in the liquid reaction composition is less than 8000 ppm.

8. A process according to claim 1 or claim 2 wherein the concentration of water in the liquid reaction composition is in the range 0.1 to 20 wt %.

9. A process according to claim 1 or claim 2 wherein the carbonylation is carried out in two reaction zones.

10. A process according to claim 3 wherein the concentration of catalyst system stabiliser in the liquid reaction composition is less than 9000 ppm.

11. A process according to claim 3 wherein the catalyst system stabiliser is selected from the group consisting of iodides or acetates of indium, cadmium, mercury, gallium and zinc.

12. A process according to claim 3 wherein the promoter is ruthenium.

13. A process according to claim 3 wherein the concentration of promoter in the liquid reaction composition is less than 8000 ppm.

14. A process according to claim 3 wherein the concentration of water in the liquid reaction composition is in the range 0.1 to 20 wt %.

15. A process according to claim 3 wherein the carbonylation is carried out in two reaction zones.

* * * * *